US012753169B2

(12) United States Patent
Tang

(10) Patent No.: US 12,753,169 B2
(45) Date of Patent: Oct. 6, 2026

(54) PREPARATION METHOD AND CHIRAL SIEVING APPLICATION OF NOVEL 12-CROWN-4 COVALENT ORGANIC FRAMEWORKS

(71) Applicant: Chongqing University of Arts and Sciences, Chongqing (CN)

(72) Inventor: Yuanzhe Tang, Chongqing (CN)

(73) Assignee: Chongqing University of Arts and Sciences, Chongqing (CN)

( * ) Notice: Subject to any disclaimer, the term of this patent is extended or adjusted under 35 U.S.C. 154(b) by 52 days.

(21) Appl. No.: 19/019,867

(22) Filed: Jan. 14, 2025

(65) Prior Publication Data

US 2026/0138972 A1 May 21, 2026

Related U.S. Application Data

(63) Continuation of application No. PCT/CN2024/140240, filed on Dec. 18, 2024.

(30) Foreign Application Priority Data

Nov. 18, 2024 (CN) ........................ 202411645771.6

(51) Int. Cl.
*C07D 405/14* (2006.01)
*C09K 11/06* (2006.01)

(52) U.S. Cl.
CPC ............ *C07D 405/14* (2013.01); *C09K 11/06* (2013.01); *C09K 2211/1048* (2013.01)

(58) Field of Classification Search
CPC .................. C07D 405/14; C09K 11/06; C09K 2211/1048
See application file for complete search history.

(56) References Cited

FOREIGN PATENT DOCUMENTS

| | | |
|---|---|---|
| CN | 117903419 A | 4/2024 |
| CN | 118221895 A | 6/2024 |

OTHER PUBLICATIONS

Bhushan et al., Comparative Application of Microwave, Ultrasonication, Ultracentrifugation and Conventional Heating for Preparation of Sample as Dinitrophenyl Derivative for Direct Enantioseparation of Certain Amino Alcohols . . . , Journal of Chromatography A, vol. 1216, No. 45, pp. 7941-7945 (Year: 2009).*
Qin et al., Covalent Organic Frameworks and Related Innovative Materials in Chiral Separation and Recognition, Biomedical Chromatography, vol. 38, No. 12, e6008 (Year: 2024).*
CNIPA, Notification of First Office Action for CN202411645771.6, Sep. 30, 2025.
Chongqing University of Arts and Sciences (Applicant), Replacement claims (allowed) of CN202411645771.6, Nov. 7, 2025.
CNIPA, Notification to grant patent right for invention in CN202411645771.6, Jan. 5, 2026.

* cited by examiner

*Primary Examiner* — Brenda L Coleman
(74) *Attorney, Agent, or Firm* — Hemisphere Law, PLLC

(57) ABSTRACT

A synthesis method for a novel covalent organic framework with a 12-crown-4 group based on chiral sieving is provided, and the novel covalent organic framework with the 12-crown-4 group is prepared, and the CCOF-HTOD-1 can be used as a fluorescent probe to achieve chiral sieving of different chiral drugs (L-PGL, D-PGL, L-PAL, D-TPL, L-TPL and D-TPL). The CCOF-HTOD-1 not only has advantages of simple preparation method, large-scale preparation, uniform structure, easy dispersion, and excellent CD optical activity, but also has excellent performance in detecting different chiral drugs, high selectivity, and recyclability, which can solve problems of difficult separation and low detection efficiency of common chiral drugs.

8 Claims, 4 Drawing Sheets

PREPARATION METHOD AND CHIRAL SIEVING APPLICATION OF NOVEL 12-CROWN-4 COVALENT ORGANIC FRAMEWORKS

TECHNICAL FIELD

The disclosure relates to the technical field of fluorescence detection, and more particularly to a preparation method and a chiral sieving application of novel 12-crown-4 covalent organic frameworks (also referred to as dodecyl crown tetraether covalent organic frameworks), in which the preparation method of the novel 12-crown-4 covalent organic frameworks is easy, and synthesis conditions of the novel 12-crown-4 covalent organic frameworks is mild.

BACKGROUND

Chirality is a fundamental characteristic of life and plays a crucial role in various chemical and biological processes. Due to many potential applications of chirality, testing chirality in various drugs is crucial. Common testing and separation methods such as asymmetric catalysis, chiral separation, and magnetism have defects of high cost and complex operation, while using fluorescence sensing for chiral sieving is an efficient and effective strategy. The use of fluorescence sensing for chiral sieving requires the preparation of chiral fluorescent materials. At present, a common strategy for preparing the chiral fluorescent materials is to use chiral modules to manufacture chiral skeleton structures. The principle is to use chiral monomers with optical activity to form chiral materials, and the inherent chirality of the monomers is converted into the chirality of the chiral materials through a process of chiral conservation. Based on the above principle and physicochemical properties of target chiral drugs, it is a feasible strategy to chemically bond functional ligands (such as crown ethers) that can interact with the target chiral drug to fluorescent probes prepared by porous materials.

Covalent organic frameworks (COFs) are an emerging class of crystalline polymers with adjustable molecular composition, structure, and function, similar to metal organic frameworks (MOFs). Compared with the MOFs, the COFs have been less developed, especially crown ether functionalized ethylene-based COFs for chiral sieving, which have not yet been developed. The currently reported ethylene-based COFs not only have high fluorescence performance, but their stability also makes them suitable for vast majority of chiral sieving scenarios. Therefore, the preparation of ligands with functional crown ether chemical bond structures and their derived ethylene-based COFs for chiral sieving is innovative and rational. Therefore, a novel 12-crown-4 covalent organic framework is prepared for chiral sieving of common chiral drugs. It is expected that this material will have high efficiency, selectivity, and recyclability for the detection of these common chiral drugs.

SUMMARY

An objective of the disclosure is to provide a synthesis method of a novel 12-crown-4 covalent organic framework based on the above method and strategy, with a goal of chiral sieving of different chiral drugs, and the chiral drugs are selected from the group consisting of L-phenylglycinol (L-PGL), D-phenylglycinol (D-PGL), L-phenylalaninol (L-PAL), D-phenylalaninol (D-PAL), L-tryptophan (L-TPL) and D-tryptophan (D-TPL). The material developed by the disclosure has advantages of high efficiency, high selectivity and recyclability for the detection of the chiral drugs, which can effectively solve disadvantages of instability and low efficiency of traditional chiral sieving materials.

Technical solutions of the disclosure are as follows.

A novel chiral covalent organic framework-2,3,5,6,8,9-hexahydrobenzo[B][1,4,7,10]tetraoxacyclododecene-11,14-diphenylaldehyde-1 (CCOF-HTOD-1) with a 12-crown-4 ($C_8H_{16}O_4$) group is prepared by the following method:

adding 2,3,5,6-tetramethylpyrazine (TMP, $C_8H_{12}N_2$), 2,3,5,6,8,9-hexahydrobenzo[B][1,4,7,10]tetraoxacyclododecene-11,14-diphenylaldehyde (HTOD, $C_{28}H_{24}O_6$), benzoic anhydride ($C_{14}H_{10}O_3$) and benzoic acid ($C_7H_6O_2$) into a 10 milliliter (mL) Schlenk reaction tube to obtain a mixed solution, shaking the mixed solution in the Schlenk reaction tube thoroughly to obtain a uniform solution, performing three times of nitrogen protection on the uniform solution to obtain a reaction system, heating the reaction system in an oven to react to thereby obtain a heated reaction system, cooling the heated reaction system after completing reaction to obtain a cooled reaction system, washing the cooled reaction system with a mixed solution of a sodium hydroxide (NaOH) solution and methanol for multiple times to obtain a first washed reaction system, washing the first washed reaction system with dimethylformamide (DMF, $C_3H_7NO$)) for multiple times to obtain a second washed reaction system, washing the second washed reaction system with ethanol for multiple times to obtain a third washed reaction system, and drying the third washed reaction system under vacuum at 100 Celsius degrees (° C.) to obtain the CCOF-HTOD-1 in yellow.

A molar ratio of the TMP to the HTOD is 1:0.1-5. A molar ratio of the HTOD to the benzoic anhydride is 1:0.1-10. A molar ratio of the benzoic anhydride to the benzoic acid is 1:0.01-50. A temperature for reacting in the oven is in a range of 100° C. to 220° C. A period for reacting in the oven is in a range of 0.1 day to 7 days.

Compared to the related art, substantive advantages of the disclosure are as follows.

(1) The preparation method is easy, and can be carried out on a large scale.

(2) The prepared novel 12-crown-4 covalent organic framework (i.e., the CCOF-HTOD-1) has a uniform structure, which is conducive to dispersion.

(3) The CCOF-HTOD-1 has excellent circular dichroism (CD) optical activity and is suitable for chiral sieving of the chiral drugs.

(4) The CCOF-HTOD-1 has advantages of high efficiency, high selectivity and recyclability for the detection of the chiral drugs.

DETAILED DESCRIPTION OF EMBODIMENTS

Figure 1:
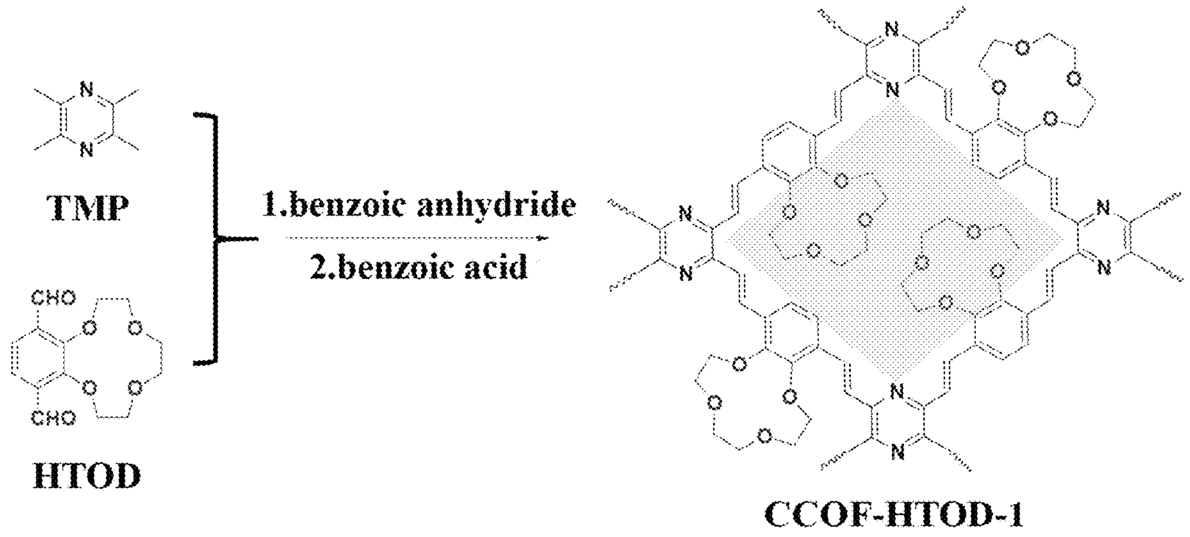
FIG. 1 illustrates a schematic structural diagram of CCOF-HTOD-1 according to an embodiment 1 of the disclosure.
Figure 2:
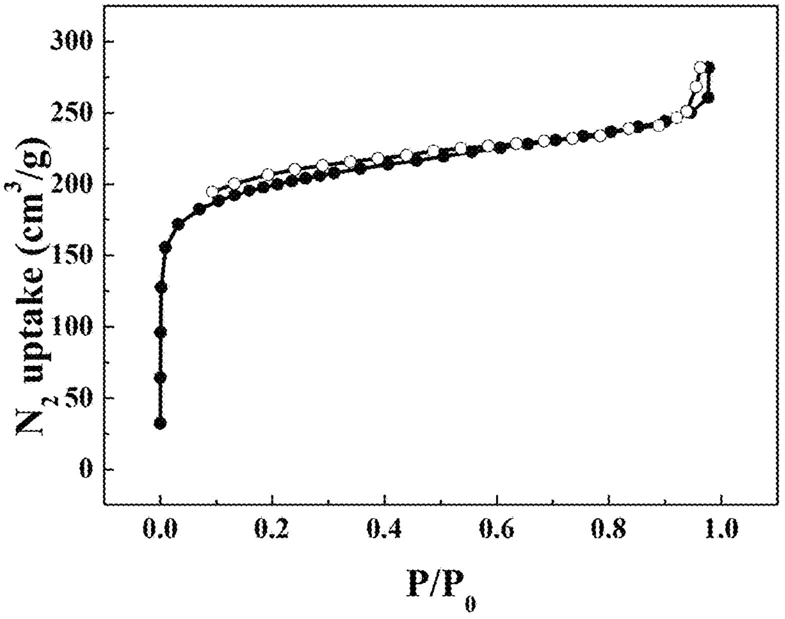
FIG. 2 illustrates a Brunauer-Emmett-Teller (BET) diagram of the CCOF-HTOD-1 according to the embodiment 1 of the disclosure.
Figure 3:
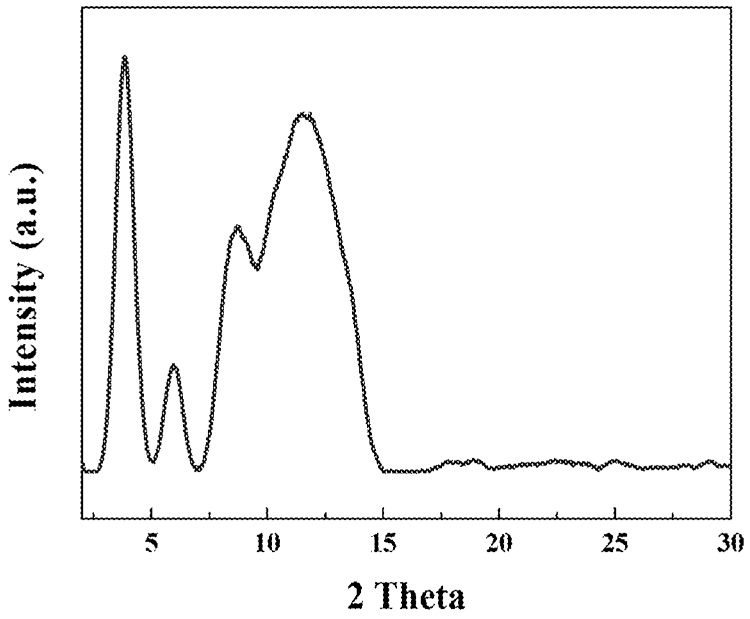
FIG. 3 illustrates an X-ray diffraction (XRD) diagram of the CCOF-HTOD-1 according to the embodiment 1 of the disclosure.
Figure 4:
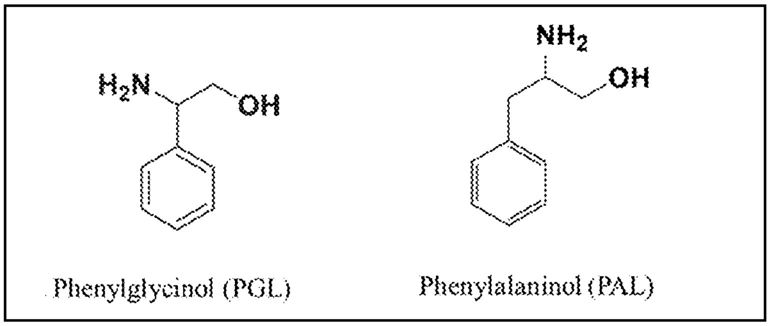
FIG. 4 illustrates a schematic structural diagram of chiral drug molecules detected by the CCOF-HTOD-1 according to the embodiment 1 of the disclosure.
Figure 5:
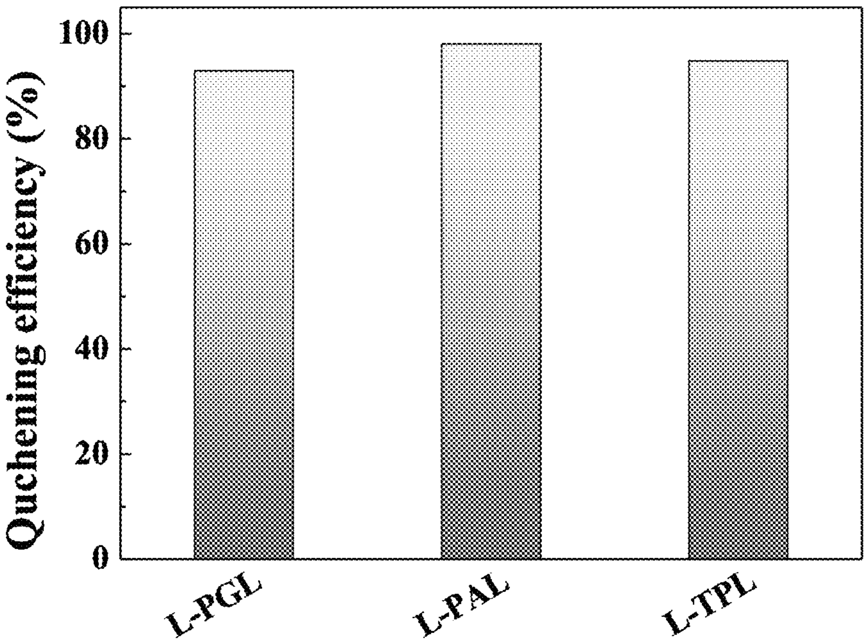
FIG. 5 illustrates a schematic diagram of detection performance of the CCOF-HTOD-1 for chiral drugs according to the embodiment 1 of the disclosure.
Figure 6:
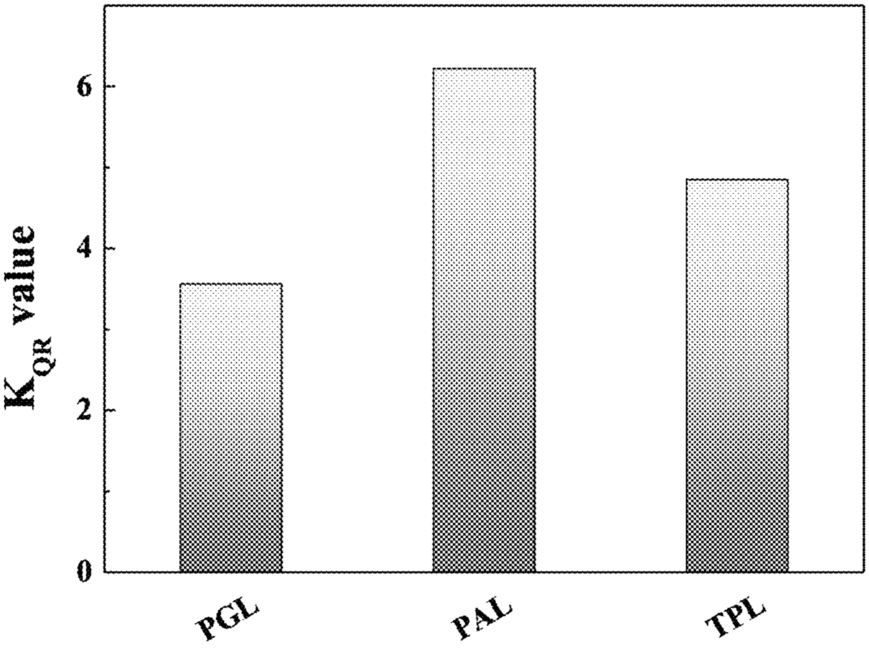
FIG. 6 illustrates a schematic diagram of selectivity of the CCOF-HTOD-1 for the chiral drugs according to a comparative embodiment 1 of the disclosure.
Figure 7:
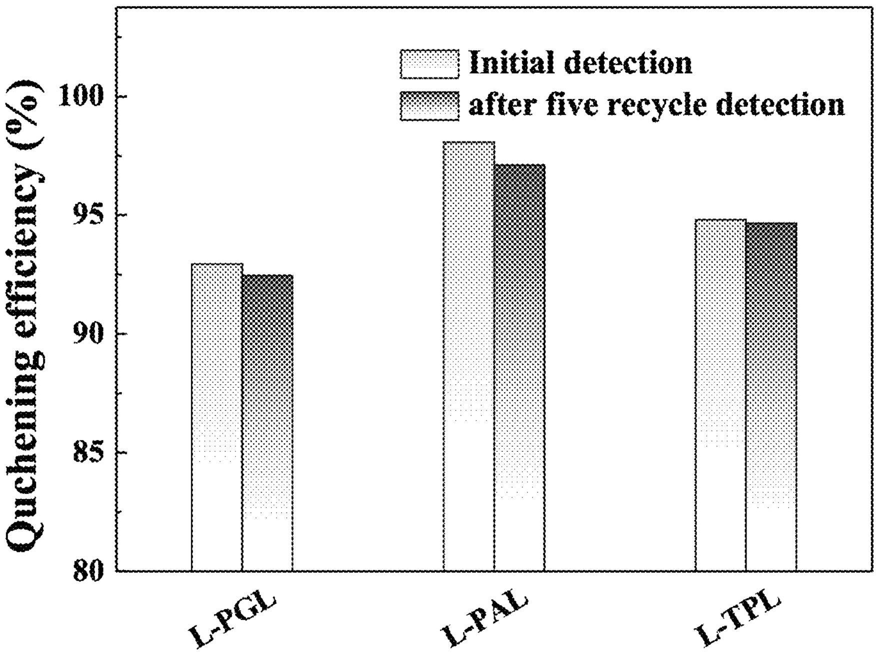
FIG. 7 illustrates a schematic diagram of cyclic detection of the CCOF-HTOD-1 for the chiral drugs according to the comparative embodiment 1 of the disclosure.

The disclosure is described in detail in conjunction with embodiments below, but the disclosure is not limited to the following embodiments. All variations and implementations should be included within the technical scope of the disclosure without departing from its content and scope.

Embodiment 1: Preparation of a CCOF-HTOD-1

TMP (0.5 millimoles abbreviated as mmol, 68.1 milligrams abbreviated as mg), HTOD (0.5 mmol, 140.1 mg), benzoic anhydride (2 mmol, 452 mg) and benzoic acid (0.2 mmol, 24.6 mg) are added into a 10 mL Schlenk reaction tube to obtain a mixed solution. The mixed solution in the Schlenk reaction tube is shaken thoroughly to obtain a uniform solution, and three times of nitrogen protection are performed on the uniform solution to obtain a reaction system. The reaction system is heated in an oven to react at 180° C. for 4 days to thereby obtain a heated reaction system, and the heated reaction system is cooled after completing reaction to obtain a cooled reaction system. The cooled reaction system is washed with a mixed solution of a NaOH solution and methanol for three times to obtain a first washed reaction system, the first washed reaction system is washed with DMF for three times to obtain a second washed reaction system, and the second washed reaction system is washed with ethanol for three times to obtain a third washed reaction system. The third washed reaction system is dried under vacuum at 100° C. to obtain the CCOF-HTOD-1 in yellow.

Embodiment 2: Preparation of the CCOF-HTOD-1

TMP (1 mmol, 136.2 mg), HTOD (0.5 mmol, 140.1 mg), benzoic anhydride (2 mmol, 452 mg) and benzoic acid (0.2 mmol, 24.6 mg) are added into a 10 mL Schlenk reaction tube to obtain a mixed solution. The mixed solution in the Schlenk reaction tube is shaken thoroughly to obtain a uniform solution, and three times of nitrogen protection are performed on the uniform solution to obtain a reaction system. The reaction system is heated in an oven to react at 180° C. for 4 days to thereby obtain a heated reaction system, and the heated reaction system is cooled after completing reaction to obtain a cooled reaction system. The cooled reaction system is washed with a mixed solution of a NaOH solution and methanol for three times to obtain a first washed reaction system, the first washed reaction system is washed with DMF for three times to obtain a second washed reaction system, and the second washed reaction system is washed with ethanol for three times to obtain a third washed reaction system. The third washed reaction system is dried under vacuum at 100° C. to obtain the CCOF-HTOD-1 in yellow.

Embodiment 3: Preparation of the CCOF-HTOD-1

TMP (0.5 mmol, 68.1 mg), HTOD (0.5 mmol, 140.1 mg), benzoic anhydride (4 mmol, 904 mg) and benzoic acid (0.2 mmol, 24.6 mg) are added into a 10 mL Schlenk reaction tube to obtain a mixed solution. The mixed solution in the Schlenk reaction tube is shaken thoroughly to obtain a uniform solution, and three times of nitrogen protection are performed on the uniform solution to obtain a reaction system. The reaction system is heated in an oven to react at 180° C. for 4 days to thereby obtain a heated reaction system, and the heated reaction system is cooled after completing reaction to obtain a cooled reaction system. The cooled reaction system is washed with a mixed solution of a NaOH solution and methanol for three times to obtain a first washed reaction system, the first washed reaction system is washed with DMF for three times to obtain a second washed reaction system, and the second washed reaction system is washed with ethanol for three times to obtain a third washed reaction system. The third washed reaction system is dried under vacuum at 100° C. to obtain the CCOF-HTOD-1 in yellow.

Embodiment 4: Preparation of the CCOF-HTOD-1

TMP (0.5 mmol, 68.1 mg), HTOD (0.5 mmol, 140.1 mg), benzoic anhydride (2 mmol, 452 mg) and benzoic acid (0.4 mmol, 49.2 mg) are added into a 10 mL Schlenk reaction tube to obtain a mixed solution. The mixed solution in the Schlenk reaction tube is shaken thoroughly to obtain a uniform solution, and three times of nitrogen protection are performed on the uniform solution to obtain a reaction system. The reaction system is heated in an oven to react at 180° C. for 4 days to thereby obtain a heated reaction system, and the heated reaction system is cooled after completing reaction to obtain a cooled reaction system. The cooled reaction system is washed with a mixed solution of a NaOH solution and methanol for three times to obtain a first washed reaction system, the first washed reaction system is washed with DMF for three times to obtain a second washed reaction system, and the second washed reaction system is washed with ethanol for three times to obtain a third washed reaction system. The third washed reaction system is dried under vacuum at 100° C. to obtain the CCOF-HTOD-1 in yellow.

Embodiment 5: Preparation of the CCOF-HTOD-1

TMP (0.5 mmol, 68.1 mg), HTOD (0.5 mmol, 140.1 mg), benzoic anhydride (2 mmol, 452 mg) and benzoic acid (0.2 mmol, 24.6 mg) are added into a 10 mL Schlenk reaction tube to obtain a mixed solution. The mixed solution in the Schlenk reaction tube is shaken thoroughly to obtain a uniform solution, and three times of nitrogen protection are performed on the uniform solution to obtain a reaction system. The reaction system is heated in an oven to react at 150° C. for 4 days to thereby obtain a heated reaction system, and the heated reaction system is cooled after completing reaction to obtain a cooled reaction system. The cooled reaction system is washed with a mixed solution of a NaOH solution and methanol for three times to obtain a first washed reaction system, the first washed reaction system is washed with DMF for three times to obtain a second washed reaction system, and the second washed reaction system is washed with ethanol for three times to obtain a third washed reaction system. The third washed reaction system is dried under vacuum at 100° C. to obtain the CCOF-HTOD-1 in yellow.

Embodiment 6: Preparation of the CCOF-HTOD-1

TMP (0.5 mmol, 68.1 mg), HTOD (0.5 mmol, 140.1 mg), benzoic anhydride (2 mmol, 452 mg) and benzoic acid (0.2 mmol, 24.6 mg) are added into a 10 mL Schlenk reaction tube to obtain a mixed solution. The mixed solution in the Schlenk reaction tube is shaken thoroughly to obtain a uniform solution, and three times of nitrogen protection are performed on the uniform solution to obtain a reaction system. The reaction system is heated in an oven to react at 150° C. for 2 days to thereby obtain a heated reaction system, and the heated reaction system is cooled after completing reaction to obtain a cooled reaction system. The cooled reaction system is washed with a mixed solution of a NaOH solution and methanol for three times to obtain a first washed reaction system, the first washed reaction system is washed with DMF for three times to obtain a second washed reaction system, and the second washed reaction system is washed with ethanol for three times to obtain a third washed reaction system. The third washed reaction system is dried under vacuum at 100° C. to obtain the CCOF-HTOD-1 in.

Embodiment 7: Test of Detection Performance of the CCOF-HTOD-1 for Chiral Drugs The CCOF-HTOD-1 (10 mg) of the embodiment 1 is weighed, ground and added into a vial containing water (20 mL) to stir with ultrasound thoroughly to thereby obtain a CCOF-HTOD-1 suspension (2 mL), and the CCOF-HTOD-1 suspension is taken out and placed into a cuvette for a fluorescence detection experiment. The chiral drug (L-PGL, D-PGL, L-PAL, D-PAL, L-TPL and D-TPL) solutions (1 millimole per liter abbreviated as mM, 20 microliters abbreviated as μL for each time) are gradually added into the CCOF-HTOD-1 suspension, and fluorescence intensity of the CCOF-HTOD-1 suspension (2 mL) is immediately measured after each addition of the chiral drug solutions, for a total of 10 times. During the whole fluorescence detection experiment, the mixed solution (i.e., the mixed solution of the CCOF-HTOD-1 suspension and the chiral drugs) is stirred at a constant rate to maintain its uniformity. It can be concluded through the fluorescence detection experiment that quenching efficiencies of the CCOF-HTOD-1 for L-type chiral drugs (L-PGL, L-PAL and L-TPL) reaches 93%, 98% and 95%, respectively, which far exceeds the detection performance of other traditional fluorescent materials for the chiral drugs.

Embodiment 8: Test of Selectivity Performance of the CCOF-HTOD-1 for Chiral Drugs A stern-volmer constant ($K_{sv}$) value of the CCOF-HTOD-1 of the embodiment 1 for the L-type chiral drugs (L-PGL, L-PAL and L-TPL) is compared with a $K_{sv}$ value of the CCOF-HTOD-1 of the embodiment 1 for D-type chiral drugs (D-PGL, D-PAL and D-TPL), PGL is taken as an example, the calculation method of a kernel quantile regression ($K_{QR}$) value is $K_{QR}=K_{sv[L\text{-}PGL]}/K_{sv[D\text{-}PGL]}$, and the higher the obtained value, the better the selectivity. The $K_{QR}$ values of the CCOF-HTOD-1 of the embodiment 1 for PGL, PAL and TPL are respectively 3.56, 6.22 and 4.85, which indicates that the CCOF-HTOD-1 has significant selectivity for the detection of PGL, PAL and TPL.

Embodiment 9: Test of Cyclic Performance of Regenerated CCOF-HTOD-1 for Chiral Drugs After the CCOF-HTOD-1 of the embodiment 1 is selected for chiral drug detection test, the CCOF-HTOD-1 that has detected the chiral drugs is taken, and is stirred with ethanol at the room temperature for 12 hours to obtain a mixed solution. The mixed solution is washed for three times, and then filtered to obtain a product. The product is dried under vacuum at 100° C. to obtain an eluted CCOF-HTOD-1 chiral drug. The CCOF-HTOD-1 chiral drug before elution and the eluted CCOF-HTOD-1 chiral drug are weighed to obtain a weight change. The eluted material is reused for the detection experiment of the chiral drugs, with at least five recycles of testing.

Maximum detection performance of the CCOF-HTOD-1 for the L-type chiral drugs can still maintain more than 99% of original maximum detection performance of the CCOF-HTOD-1 after five recycle detection.

Of course, the above embodiments are merely a detailed description of the corresponding technical solutions of the disclosure, and are not limited to the above embodiments. For those skilled in the art, various changes or modifications can still be made based on the above embodiments. Not all implementation methods are listed here, and any changes or modifications derived from principles or mechanisms similar to those mentioned above are within the scope of protection of the disclosure.

What is claimed is:

1. An application method of a chiral covalent organic framework-2,3,5,6,8,9-hexahydrobenzo[B][1,4,7,10]tetraoxacyclododecene-11,14-diphenylaldehyde-1 (CCOF-HTOD-1) with a 12-crown-4 group in detection of a chiral drug, wherein a covalent organic framework (COF) with the 12-crown-4 group is prepared by the following steps:

adding 2,3,5,6-tetramethylpyrazine (TMP), 2,3,5,6,8,9-hexahydrobenzo[B][1,4,7,10] tetraoxacyclododecene-11,14-diphenylaldehyde (HTOD), benzoic anhydride and benzoic acid into a 10 mL Schlenk reaction tube to obtain a mixed solution, shaking the mixed solution in the Schlenk reaction tube thoroughly to obtain a uniform solution, performing three times of nitrogen protection on the uniform solution to obtain a reaction system, heating the reaction system in an oven to react to thereby obtain a heated reaction system, cooling the heated reaction system after completing reaction to obtain a cooled reaction system, washing the cooled reaction system with a mixed solution of a sodium hydroxide (NaOH) solution and methanol for multiple times to obtain a first washed reaction system, washing the first washed reaction system with dimethylformamide (DMF) for multiple times to obtain a second washed reaction system, washing the second washed reaction system with ethanol for multiple times to obtain a third washed reaction system, and drying the third washed reaction system under vacuum at 100° C. to obtain the CCOF-HTOD-1 in yellow; and wherein the chiral drug is L-Phenylglycinol (L-PGL), or L-Phenylalaninol (L-PAL).

2. The application method as claimed in claim 1, wherein a molar ratio of the TMP to the HTOD is 1:0.1-5.

3. The application method as claimed in claim 1, wherein a molar ratio of the HTOD to the benzoic anhydride is 1:0.1-10.

4. The application method as claimed in claim 1, wherein a molar ratio of the benzoic anhydride to the benzoic acid is 1:0.01-50.

5. The application method as claimed in claim 1, wherein a temperature for reacting in the oven is in a range of 100° C. to 220° C.

6. The application method as claimed in claim 1, wherein a period for reacting in the oven is in a range of 0.1 day to 7 days.

7. The application method as claimed in claim 1, wherein kernel quantile regression ($K_{QR}$) values of the CCOF-HTOD-1 for L-PGL and L-PAL are respectively 3.56 and 6.22.

8. The application method as claimed in claim 1, wherein maximum detection performance of the CCOF-HTOD-1 for L-type chiral drugs maintains more than 99% of original maximum detection performance of the CCOF-HTOD-1 after five recycle detection.

* * * * *